United States Patent [19]

Orazio et al.

[11] 4,022,531
[45] May 10, 1977

[54] MONOCHROMATOR

[75] Inventors: Svelto Orazio, Segrate; Cubeddu Rinaldo; Zagara Federico, both of Milan; Mengarelli Quirino; Riccardi Clemente, both of Monza (Milan), all of Italy

[73] Assignee: U.S. Philips Corporation, New York, N.Y.

[22] Filed: Dec. 4, 1975

[21] Appl. No.: 637,778

Related U.S. Application Data

[63] Continuation of Ser. No. 517,403, Oct. 24, 1974, abandoned.

[30] Foreign Application Priority Data

Oct. 17, 1973 Italy .................. 30228/73

[52] U.S. Cl. ............................. 356/100
[51] Int. Cl.² ......................... G01J 3/14
[58] Field of Search .......... 356/51, 94, 93, 97, 356/99–101

[56] References Cited

UNITED STATES PATENTS

| | | | |
|---|---|---|---|
| 2,879,393 | 3/1959 | Cary et al. | 356/94 |
| 3,218,914 | 11/1965 | Bartz et al. | 356/97 |
| 3,279,308 | 11/1966 | Bartz et al. | 356/51 |
| 3,521,960 | 7/1970 | Newcomer | 356/100 X |
| 3,522,739 | 8/1970 | Coor et al. | 356/97 |
| 3,554,649 | 1/1971 | Ridgway | 356/100 |

Primary Examiner—John K. Corbin
Assistant Examiner—F. L. Evans
Attorney, Agent, or Firm—Frank R. Trifari; Simon L. Cohen

[57] ABSTRACT

A monochromator provided with a plurality of entrance windows for beams of white light emitted by respective lamps which are alternately operated. The internal optics of the monochromator consist of a dispersing system disposed so that each of the beams of white light is intercepted and converted into dispersed light which is composed of discrete monochromatic light beams of different wavelengths. The monochromator has an exit window with a slit of predetermined dimensions so as to transmit only one wavelength at a time.

6 Claims, 3 Drawing Figures

MONOCHROMATOR

This is a continuation of application Ser. No. 517,403, filed Oct. 24, 1974, now abandoned.

The present invention relates to a monochromator, i.e. a device which enables the production of monochromatic light of various wavelengths from polychromatic white ligth.

Monochromators have various fields of application but are used in particular as essential components of spectrophotometers for performing spectral photometric analysis of sample cells; an example is the examination of water for the presence of dissolved organic materials which may render the water turbid.

The monochromators used at present generally comprise a box-shaped member which is provided with entrance windows through which the white light emitted by a lamp can pass. The box-shaped member contains an optical prism or another dispersing system on which the white light is incident and which by means of the known refraction phenomena produces a spectrum of the wavelengths which depends upon the characteristics of the lamp used. The monochromatic light beams from which this spectrum is composed are usually directed by means of mirrors to an exit window which has a selection slit which allows only the beam corresponding to a given wavelength to pass. Thus the light emerging from the box-shaped member is monochromatic light having a wavelength which depends upon the position of the exit slit.

In order to vary the wavelength of the monochromatic light which emerges from the monochromator, hitherto systems have generally been used which are capable of producing variations, of the order of magnitude of microns, in the angular position of the prism (or in general of the dispersing system), or systems capable of producing transverse displacements of the exit slit which are of the order of microns.

Both methods have the disadvantage that the monochromator must be equipped with mechanical moving members which greatly contribute to increasing the cost and the complexity of operation of the monochromator and which require frequent maintenance.

Hence it is an object of the present invention to provide a monochromator in which the variation of the wavelength of the monochromator light produced is obtained in a simple and rapid manner without the use of moving mechanical members.

According to the invention this is obtained by means of a monochromator which is characterized by a box-shaped member provided with a plurality of entrance windows for beams of white light emitted by respective lamps which are alternately operated, the box-shaped member further containing a dispersing system disposed within the box so that each of the said beams of white light is intercepted and converted into dispersed light which is composed of discrete monochromatic light beams of different wavelengths, the box further having an exit window provided with a slit of a size such as to allow only one of the said monochromatic light beams to pass, means being provided for directing the said beams of white light to a dispersing system so that the light beams are incident on this dispersing system each at a different angle of incidence, with the result that at the exit a light spectrum is obtained which diverges in accordance with the relevant angle of incidence so that the wavelength of the beam of monochromatic light transmitted by the slit varies as a function of the identity of the relevant lamp.

It will be clear that a monochromator according to the invention provides the desired variation of the wavelength of the monochromatic light without the need for moving mechanical members, simply by switching on one of a plurality of lamps. This obviously results in simpler design and reduced cost. The necessity of periodically maintaining the device is also reduced appreciably owing to the well-known long average lives of the lamps. Furthermore, modulation of the white light, which frequently is required when the monochromator forms part of a spectrophotometer, can be performed in a far simpler manner: it is sufficient to control a train of pulses for the various lamps by electronic means. Finally it should be mentioned, also with regard to a specific use in a spectrophotometer, that two or more lamps may sequentially be operated by electronic means in order to obtain differential spectra.

An embodiment of the invention will now be described, by way of example, with reference to the accompanying diagrammatic drawings, in which.

Figure 1:
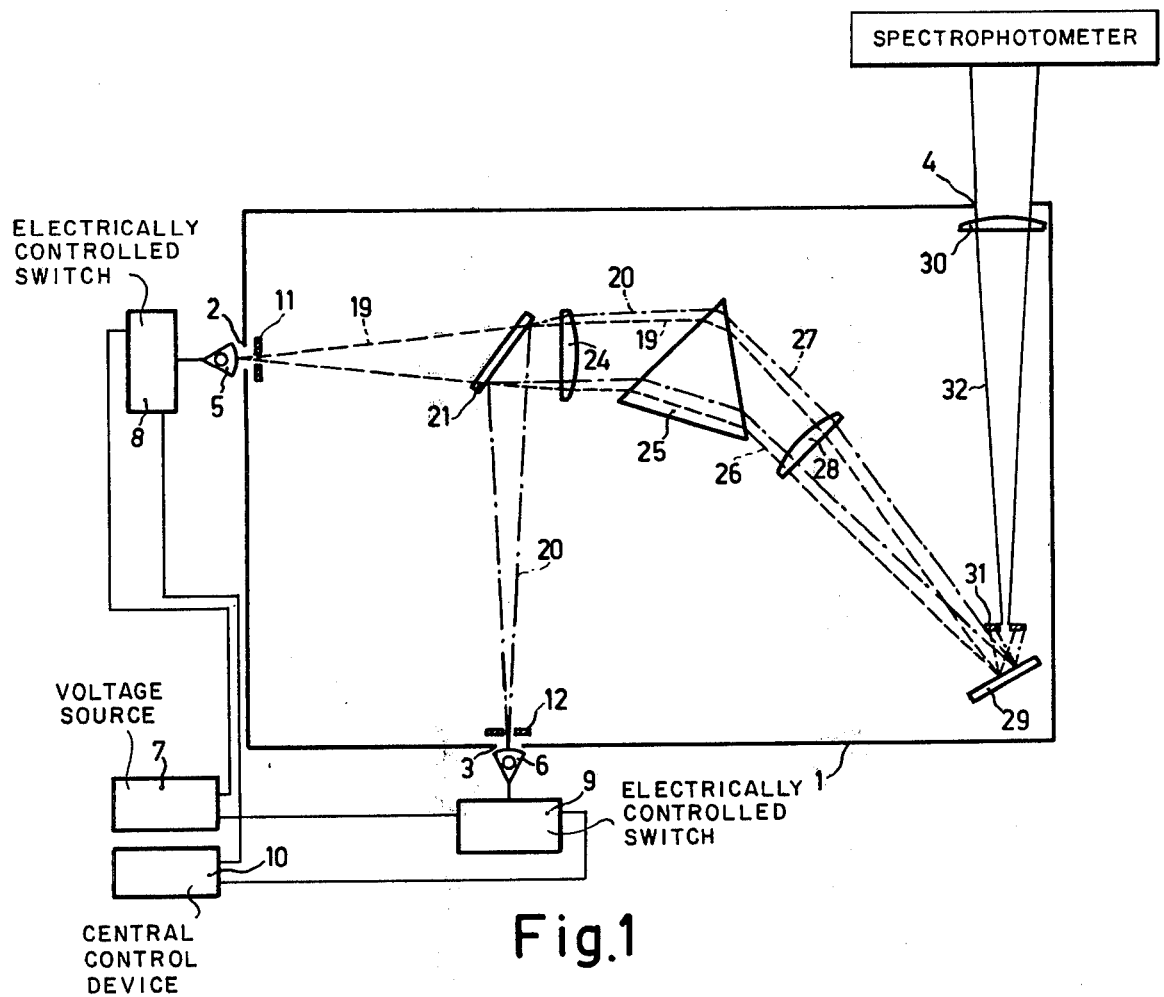
FIG. 1 shows schematically a monochromator according to the invention.

The monochromator shown in FIG. 1 has a box-shaped casing 1 provided with two entrance windows 2 and 3 and an exit window 4. Externally of the casing 1 two lamps 5 and 6 which emit white light are arranged which are associated with the entrance windows 2 and 3 respectively and can alternately be fed, either continuously or pulsatorily, by a voltage source 7 which is controlled by two switches 8 and 9 which in turn are controlled by a central control device 10. Internally of the casing 1 two slits 11 and 12 are associated with the entrance windows 2 and 3 respectively, which slits are suitable for obtaining the required efficiency and bandwidth characteristics at the exit.

Figure 2:
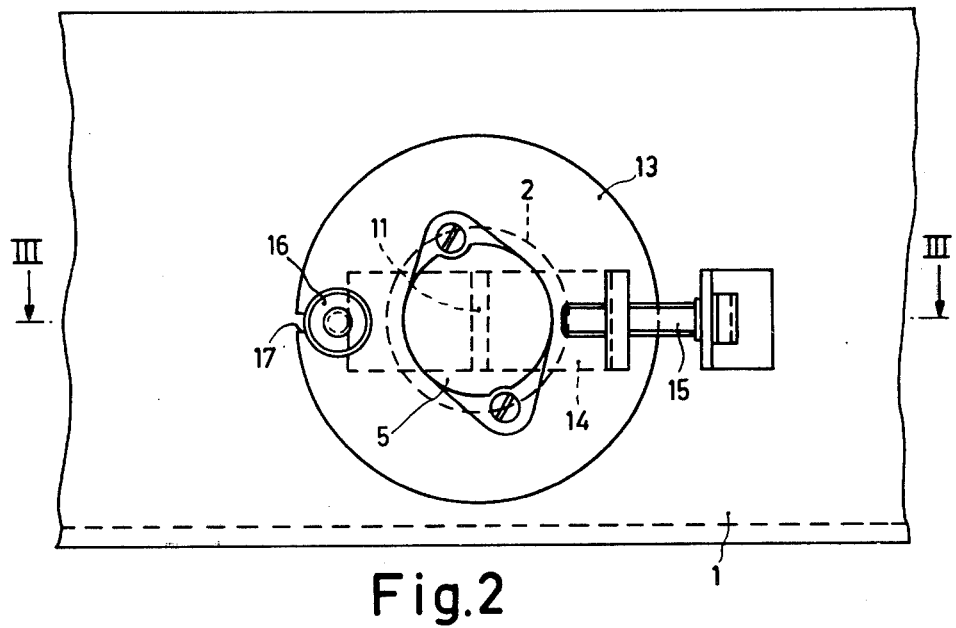
FIG. 2 shows on an enlarged scale an embodiment of the entrance windows.
Figure 3:
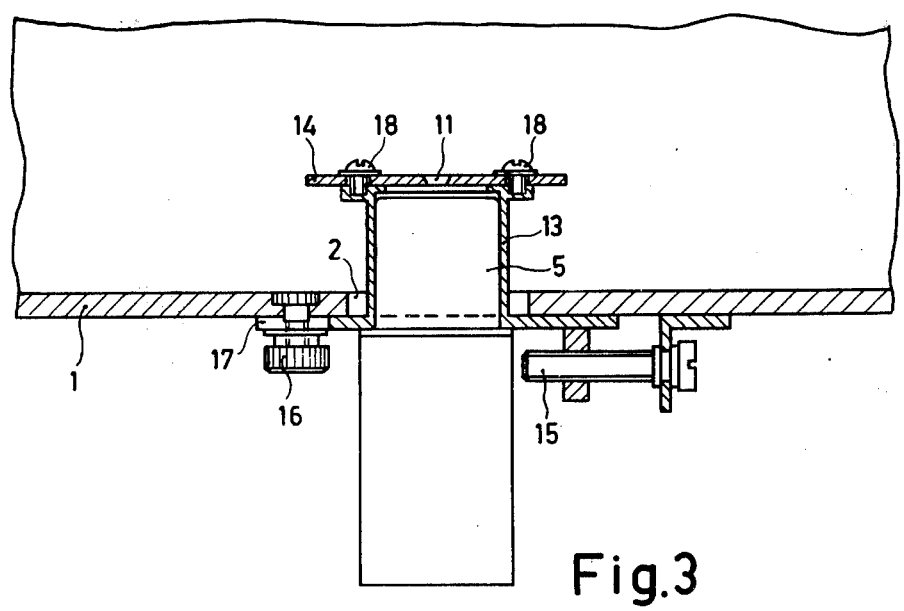
FIG. 3 is a sectional view taken on the line III—III of FIG. 2.

An embodiment of the association of a window and a slit is shown in FIGS. 2 and 3 which relate to the window 2 and the slit 11. In the embodiment shown the lamp 5 is inserted into a socket 13 which also carries a plate 14 in which the slit 11 is formed. The socket 13 is partly inserted into the window 2 and is secured to, and adapted to be laterally displaced with respect to, the casing 1 by means of a set screw 15 and a clamping screw 16 the shank of which is inserted into a slot 17 in the socket 13. Thus by altering the clamping 16 and tightening or releasing the set screw 15 the lamp-and-slit assembly can be displaced to the right or to the left so that in practice the dispersing system can be adjusted so that the axis of the beam of white light passes through the slit 11.

Because the slit is secured to the socket 13 by means of screws 18 only, it may readily be interchanged with a slit of different width. The configuration of the entrance window 3 and the associated slit 12 is similar. Internally of the casing 1 a semitranparent mirror 21, which reflects and transmits equal parts of the incident light, is disposed so that both the beam of white light 19 emitted by the lamp 5 and the beam of white light 20 emitted by the lamp 6 impinge on it. Owing to the inclined position of the mirror 21 and its transmissive and reflective properties in the downward direction the two beams 19 and 20 (which are indicated by a broken line and a dot-dash line respectively) will both diverge but will be slightly displaced with respect to one another.

After the beams have traversed a collimation lens 24 so that they each become parallel (but still are inclined at a small angle to one another) they impinge on a dispersing system in the form of an optical prism 25 which converts them into dispersed light beams 26 and 27 which each, owing to the known refractive properties of optical prisms, are composed of a plurality of separate beams of monochromatic light of different wavelengths.

The dispersed beams 26 and 27 are rendered convergent by a focussing lens 28 which directs them to a totally reflecting mirror 29 at which they are reflected to the exit window 4 after traversing a plano-convex lens 30 and a suitably proportioned slit 31 so that light of a single wavelength is obtained (actually the emerging light will have a very narrow wavelength band of a width of, say, 50 A which in general will be suitable for the intended use).

Because the beams of white light 19 and 20 are incident on the prism 25 at different angles so that the monochromatic beams of which the dispersed light 26 is composed are slightly shifted with respect to those of which the dispersed light 27 is composed, the wavelength of the beam of monochromatic light which passes through the slit 31 will depend on whether the light in the casing belongs to the beam 19 or to the beam 20 and consequently whether the lamp 5 or the lamp 6 is switched on.

It will be clear that by simply operating either of the lamps 5 and 6 (by means of the central operating device 10 and the switches 8 and 9) beams of monochromatic light of different wavelengths are obtainable at the exit.

There are no moving members but only electronic members, which may readily and rapidly be switched, require substantially no maintenance and greatly simplify design, with consequent reduction in cost.

It will further be appreciated that the white light emitted by the two lamps may be modulated at will, and that the lamps may be switched on sequentially by suitable known adjustment of the central operating unit 10 (which may be in the form of a real programming unit).

Finally it should be mentioned that the monochromator of FIG. 1 which provides a choice between two wavelengths may obviously be changed, by means of small modifications, into an apparatus providing a choice between an arbitrary number of wavelengths. The only modifications required for this purpose are: increasing the number of entrance windows each associated with a lamp which emits white light, and providing further light-deflecting means in the casing 1 so that all the beams of white light are directed to the prism 25 on which they are incident at different angles which also differ from the angles of incidence of the beams 19 and 20 in FIG. 1.

What is claimed is:

1. Monochromator, comprising a plurality of white-light producing lamps having substantially the same frequency range, a box-shaped casing which is provided with a plurality of spatially separated entrance windows for beams of white light which each are emitted by one of said lamps, electronic means for selectively switching each lamp on, the casing further containing a dispersing means disposed internally of the casing so that each of the said beams of white light is incident on the dispersing means for converting said beams into dispersed light in the form of separate beams of monochromatic light of various wavelengths, a beam splitter aligned with the path of the beams from the entrance windows and aligned with the dispersing means for directing the beams from each of the entrance windows to the dispersing means along diverging light paths, the casing being further provided with an exit window provided with a slit which is proportioned so that only one of the said beams of monochromatic light is transmitted, means being provided to direct the white light to the dispersing means at a particular angle of incidence so that dispersed light is obtained which is composed of beams of monochromatic light which are inclined to light beams of the same wavelength which are emitted by another lamp so that the identity and hence the wavelength of the selected beams of monochromatic light which emerge from the exit slit are varied in accordance with the identity of the particular lamp which is switched on.

2. Monochromator as claimed in claim 1, wherein each entrance window is provided with a suitably proportioned selection slit for transmitting a sufficient amount of luminous energy.

3. Monochromator as claimed in claim 1 wherein each entrance window is provided with an entrance slit, and means for varying the position of the said entrance slit relative to the relevant entrance window.

4. Monochromater as claimed in claim 1, wherein each entrance window is provided with an entrance selection slit and means for varying the dimensions of the said entrance selection slit.

5. Monochromator as claimed in claim 1, wherein said dispersing means comprises a prism.

6. Monochromator as claimed in claim 1 further provided with a spectrophotometer in the path of the beam passing from said exit window.

* * * * *